United States Patent [19]
Lample

[11] 3,948,477
[45] Apr. 6, 1976

[54] SCREW CLAMP FOR FLEXIBLE TUBING

[75] Inventor: Esteban Torres Lample, Guadalajara, Mexico

[73] Assignee: United States Surgical Corporation, New York, N.Y.

[22] Filed: July 2, 1973

[21] Appl. No.: 375,358

[52] U.S. Cl. ............... 251/8; 16/114 A; 24/135 N; 81/177 R; 128/214 R
[51] Int. Cl.² .......................................... F16K 7/06
[58] Field of Search .......................... 251/4, 6–10; 24/135 R, 135 N, 243 B; 16/114 A, 114 B; 294/27, 103; 128/346, 214 R; 339/108 R, 108 TP, 110 R; 292/305, DIG. 30, DIG. 63; 239/526

[56] References Cited
UNITED STATES PATENTS

| | | | |
|---|---|---|---|
| 2,653,787 | 9/1953 | Myrick | 251/10 |
| 2,989,250 | 6/1961 | Simon | 239/526 X |
| 3,042,067 | 7/1962 | Hidding | 251/8 X |
| 3,332,439 | 7/1967 | Burke | 251/8 X |

FOREIGN PATENTS OR APPLICATIONS
873,413  7/1961  United Kingdom ..................... 251/8

*Primary Examiner*—Martin P. Schwadron
*Assistant Examiner*—Richard Gerard
*Attorney, Agent, or Firm*—Fleit & Jacobson

[57]         ABSTRACT

A screw clamp for clamping a flexible tubing includes a handle having a screw housing attached to one end. The housing has apertures in opposed side walls through which the flexible tubing can be passed, a base for supporting one surface of the tubing, and a bore above the base having internal screw threads in the wall thereof. A thumbscrew is threaded in the bore and defines a variable opening with the base. The handle is adapted to be gripped by the middle, ring and small fingers of the hand so that the thumbscrew can be rotated with the thumb and forefinger of the same hand to clamp the flexible tube against the base of the screw housing.

4 Claims, 4 Drawing Figures

3,948,477

SCREW CLAMP FOR FLEXIBLE TUBING

BACKGROUND OF THE INVENTION

The present invention relates to an improved screw clamp, particularly for use in intravenous parenteral fluid feeding systems.

Intravenous sets for the introduction of parenteral solution through venipuncture typically include a piercer for insertion into a parenteral solution container, a flexible plastic tube such as polyvinylchloride for transporting the parenteral fluid from the solution container to the patient, and a needle adapter to which an intravenous needle is attached. The typical intravenous set also includes a clamp which closes the internal bore of the flexible tubing to control the flow rate of the parenteral fluid. The flow rate is determined by a fluid flow meter such as a drip chamber positioned intermediate the piercer and the needle adapter and upstream of the clamp.

In using the intravenous set, the clamp is closed, the piercer fully inserted into the solution container and the container appropriately suspended. The flow of parenteral fluid is started such as by squeezing the drip chamber until it is partially full and then the intravenous needle is attached to the needle adapter. The clamp is then opened to allow parenteral solution to displace air in the tubing, meter and needle. Subsequently, the clamp is closed and the venipuncture performed. The flow of parenteral fluid is adjusted by using the clamp and the flow rate determined using the fluid flow meter.

Several different types of clamps and other valvetype elements for use with flexible tubing are known to the art. These include screw clamps, lever clamps and cam clamps, all of which act to close the internal bore of the tubing and thereby selectively prevent the passage of fluid. Known clamps, however, are difficult to handle since they typically require the use of both hands to adjust the compression of the tubing. This is particularly disadvantageous when the clamp is used with an intravenous set requiring a multiplicity of operations as outlined above. Accordingly, it would be advantageous to have a clamp which could quickly and easily be operated using only one hand, leaving the other hand free to perform other functions which may be required such as in the operation of the fluid flow meter in the intravenous set. Many known clamps are also complicated and difficult to manufacture and accordingly relatively expensive, and so these clamps are not well suited for use with an intravenous set which is discarded after one use.

In view of the foregoing, an object of the present invention is to provide an improved screw clamp for clamping a flexible tubing which is particularly suited for use in an intravenous parenteral fluid feeding system.

A further object of the present invention is to provide a clamp which can be quickly and easily operated using only one hand and can, if desired, be easily moved longitudinally of the tubing to adjust the clamping position thereon.

Still another object of the present invention is to provide an economical clamp which can be easily fabricated and will carry out the other objects of the invention.

SUMMARY OF THE INVENTION

The invention relates to a screw clamp for flexible tubing including a handle having a screw housing attached to one end. The handle and screw housing are preferably of unitary construction and formed from a moldable plastic. The screw housing has apertures in opposed side walls thereof through which the flexible tubing can be passed, a base for supporting one surface of the tubing, and a bore above the base having internal screw threads in the wall thereof. A thumbscrew, also preferably formed from a moldable plastic, is threaded in the bore and defines a variable opening with the base. The handle is adapted to being gripped by the middle, ring and small fingers of the hand so that the thumbscrew can be rotated with the thumb and forefinger of the same hand to clamp the flexible tube against the base of the screw housing.

More specifically, the screw housing comprises a rectangular prism having a base providing a rigid surface against which the tubing can be compressed by the thumbscrew. The apertures through which the tubing can be passed are provided adjacent the base of the rectangular prism. The bore comprises a cylindrical hole having partial screw threads on one side of the wall thereof disposed in the center of the rectangular prism above the base. Apertures formed in the side walls of the prism during molding form means for viewing the tubing and the position of the thumbscrew.

The thumbscrew has a cylindrical top portion adapted to being gripped by the thumb and forefinger, a threaded intermediate portion for threading into the internal screw threads of the bore of the screw housing, and an unthreaded portion having a substantially flat base for contacting and compressing the tubing. The handle is relatively flat and is slightly inclined upwards so that when gripped, the thumb and forefinger will be at the appropriate level for gripping the thumbscrew. The rear portion of the handle is of a generally rectangular shape having three grooves in the lower part thereof which can be easily gripped by the middle, ring and small fingers.

DESCRIPTION OF THE PREFERRED EMBODIMENTS

Figure 1:
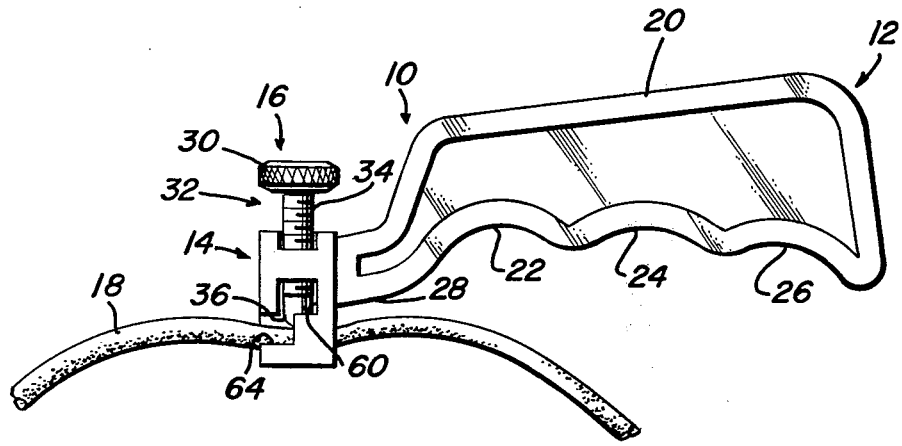
FIG. 1 is a side elevational view of the screw clamp of this invention with a flexible tubing shown passing therethrough.
Figure 2:
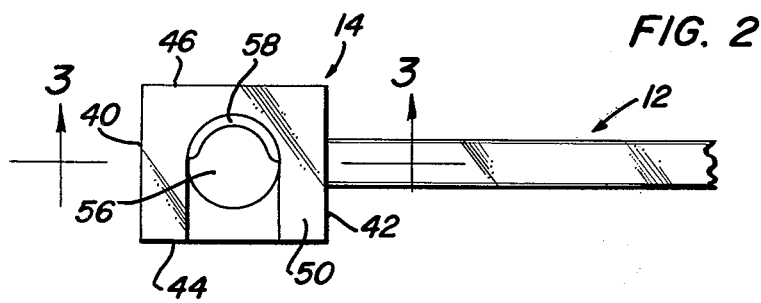
FIG. 2 is a partial top view of the screw clamp of FIG. 1.
Figure 3:
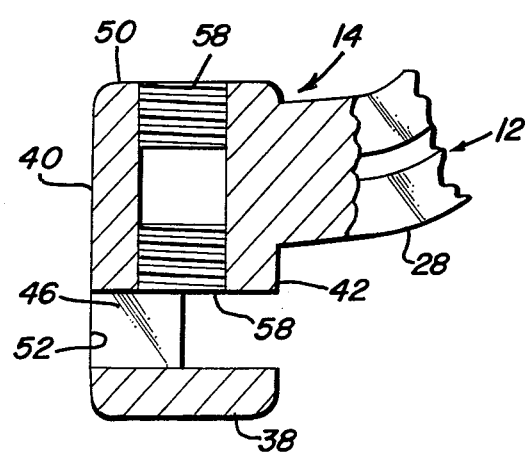
FIG. 3 is a partial vertical cross-sectional view of the screw clamp taken along lines 3—3 of FIG. 2.
Figure 4:
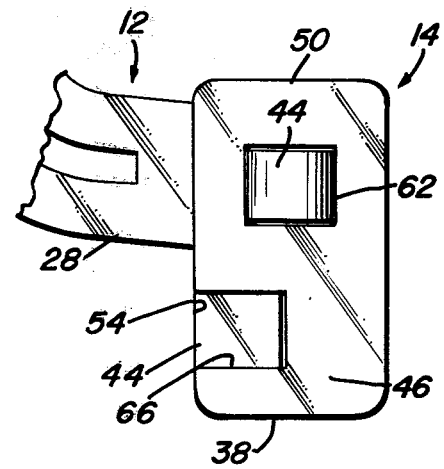
FIG. 4 is a partial rear elevational view of the screw clamp.

Referring to FIG. 1, screw clamp 10 comprises handle 12 having screw housing 14 attached to one end thereof. Thumbscrew 16 is threaded in screw housing 14 and can be rotated to clamp flexible tubing 18 against a portion of screw housing 14, thereby selectively preventing the passage of fluid through tubing 18. Handle 12 and screw housing 14 are preferably of unitary construction and are, along with thumbscrew 16, preferably formed from a moldable plastic such as nylon, polypropylene or styrene-acrylonitrile using injection molding techniques.

Handle 12 is a relatively flat, plastic plate and has generally rectangular rear portion 20 which is of suitable size and shape for being gripped by the hand. The bottom of rear portion 20 has three grooves 22, 24 and 26 formed therein which are adapted to being gripped by the middle, ring and small fingers of the hand, respectively. As can easily be seen in FIG. 1, the top of rear portion 20 is positioned above thumbscrew 16. Also, the top of rear portion 20 is slightly inclined upwards to form a small angle with respect to the horizontal. This positioning and inclination of the rear portion of handle 12 enables the thumb and forefinger to easily grip thumbscrew 16 when handle 12 is gripped by the hand. Front portion 28 of handle 12 is offset from rear portion 20 and is of considerably reduced width at the point where handle 12 and screw housing 14 meet.

Thumbscrew 16 has upper cylindrical portion 30 which is of convenient size and shape for being gripped by the thumb and forefinger. Thumbscrew 16 also includes shaft 32 which has threaded middle portion 34 which is threaded into screw housing 14 and unthreaded lower portion 36 having a substantially flat end which is adapted to contact and compress flexible tubing 18.

Referring now to FIGS. 1–4, screw housing 14 is of unitary construction and comprises a rectangular prism having base wall 38, opposed front and rear side walls 40 and 42, respectively, through which flexible tubing 18 passes, opposed side walls 44 and 46 having apertures therein for observing flexible tubing 18 and various portions of shaft 32 of thumbscrew 16, and top wall 50 through which thumbscrew 16 passes. Flexible tubing 18 can be passed through aperture 52 in front side wall 40 and aperture 54 in rear side wall 42 of screw housing 14, both of which are adjacent to base wall 38. This relationship is best seen in FIG. 1. The upper surface of base wall 38 is flat and provides a rigid base portion for supporting one surface of flexible tubing 18.

The upper portion of screw housing 14 has bore or cylindrical hole 56 passing therethrough. Partial screw threads 58 are formed in the wall of bore or cylindrical hole 56 on one side thereof. Thumbscrew 16 is threaded into bore or cylindrical hole 56 with threads 34 thereof engaging partial threads 58. Aperture 60 is formed in side wall 44 of screw housing 14 and aperture 62 in side wall 46 during molding and can be used for observing the position of threaded portion 34 of thumbscrew 16. In like manner, apertures 64 and 66 are formed in front wall 44 and rear wall 46, respectively, of screw housing 14 and can be used for observing the clamping of flexible tubing 18 by unthreaded portion 36 of thumbscrew 16. Apertures 64 and 66 are of similar shape, aperture 64 being in the front lower portion of wall 44 and aperture 66 being in the rear lower portion of wall 46. Accordingly, the inner surface of side wall 46 is adjacent tubing 18 in the front half of screw housing 14 and the inner surface of side wall 44 in the rear half.

In operation, flexible tubing 18, such as the flexible plastic tubing used in intravenous sets for the introduction of parenteral solutions through venipuncture, is threaded through screw housing 14 via openings 52 and 54 in opposed side walls 40 and 42, respectively. Handle 12 is gripped with the middle, ring and index fingers placed in grooves 22, 24 and 26, respectively. Thumbscrew 16 is then rotated to vary the opening between the upper surface of base wall 38 and the end 36 of thumbscrew 16. Accordingly, flexible tubing 18 is clamped against the upper surface of base wall 38 and the flow rate therethrough appropriately adjusted. With this arrangement, the other hand of the screw clamp operator is free to perform other necessary functions. Also, screw clamp 10 is, if desired, easily and quickly adjusted longitudinally relative to flexible tubing 18 by merely partially unthreading thumbscrew 16 and moving screw clamp 10 relative to flexible tubing 18 while holding the flexible tubing in the other hand.

As a further example of its usefulness, the screw clamp of the present invention is particularly suitable for clamping the multilumen parenteral fluid flow controller disclosed in commonly assigned copending application Ser. No. 228,213, filed Feb. 22, 1972, for "Multi-Passage Fluid Flow Control System", by B. L. Smith and now U.S. Pat. No. 3,805,830. This commonly assigned application discloses a section of flexible tubing in an intravenous set having a plurality of generally parallel, longitudinally extending flow passages formed from a resilient material such as an elastomer (e.g., a rubber or the like) in combination with a clamp for clamping the tubing section to control the parenteral fluid flow rate.

It will be appreciated that only the preferred embodiment of the inventive screw clamp has been disclosed herein and that there are other screw clamp arrangements falling within the scope of the present invention and which will be obvious to those of ordinary skill in the art.

I claim:

1. A screw clamp for use in an intravenous set having a screw clamp for clamping the flexible tubing for transporting parenteral fluid from the parenteral fluid container to the patient, the improvement comprising a screw clamp having a handle of suitable size and shape for being gripped by the middle, ring and small fingers of the hand, said handle including a relatively flat plate having a generally rectangularly shaped portion adapted to being gripped by said hand; a screw housing attached to said handle and comprising a rectangular prism having a base with a flat surface adapted to support one surface of said tubing, apertures formed in opposed side walls of said prism adjacent the flat surface of said base through which said flexible tubing can be passed, and a bore spaced from the flat surface of said base having internal screw threads in a wall portion thereof; and a thumbscrew threaded in said bore and defining a variable opening with said base, said thumbscrew having a cylindrical portion adapted to being grasped by said thumb and forefinger, a shaft having a threaded portion for engaging the internally threaded portion of said screw housing and an unthreaded end portion having a substantially flat bottom surface for contacting and clamping said flexible tubing, said thumbscrew adapted to being rotated with the thumb and forefinger of the hand gripping said handle to clamp the flexible tube against the flat surface of said base and vary the flow rate of fluid flowing therethrough, said handle, said screw housing, and said thumbscrew being formed from moldable plastic and said handle and said screw housing being of unitary construction.

2. The screw clamp of claim 1 in which a part of said handle is slightly inclined at a small angle so that said thumbscrew can be more easily gripped by said thumb and forefinger.

3. The screw clamp of claim 1 in which said screw housing has apertures therein for observing the position of said thumbscrew.

4. The screw clamp of claim 1 in which said screw housing is attached to said handle so that said handle is substantially parallel to the flexible tubing when the flexible tubing is passed through the apertures in the opposed side walls of the screw housing.

* * * * *